(12) United States Patent
Yagi et al.

(10) Patent No.: US 11,172,983 B2
(45) Date of Patent: Nov. 16, 2021

(54) BALLOON ABLATION CATHETER AND BALLOON ABLATION CATHETER SYSTEM

(71) Applicant: Toray Industries, Inc., Tokyo (JP)

(72) Inventors: Takahiro Yagi, Otsu (JP); Motoki Takaoka, Otsu (JP); Akinori Matsukuma, Otsu (JP)

(73) Assignee: Toray Industries, Inc., Tokyo (JP)

( * ) Notice: Subject to any disclaimer, the term of this patent is extended or adjusted under 35 U.S.C. 154(b) by 877 days.

(21) Appl. No.: 14/777,634

(22) PCT Filed: Mar. 28, 2014

(86) PCT No.: PCT/JP2014/059181
§ 371 (c)(1),
(2) Date: Sep. 16, 2015

(87) PCT Pub. No.: WO2014/157633
PCT Pub. Date: Oct. 2, 2014

(65) Prior Publication Data
US 2016/0287323 A1    Oct. 6, 2016

(30) Foreign Application Priority Data

Mar. 28, 2013 (JP) .............................. JP2013-068479

(51) Int. Cl.
*A61B 18/14*    (2006.01)
*A61M 25/00*    (2006.01)
*A61B 18/04*    (2006.01)
*A61B 18/00*    (2006.01)

(52) U.S. Cl.
CPC .. *A61B 18/1492* (2013.01); *A61B 2018/0016* (2013.01); *A61B 2018/0022* (2013.01);
(Continued)

(58) Field of Classification Search
CPC ............ A61M 25/0026; A61M 25/005; A61B 18/1492; A61B 2018/0016;
(Continued)

(56) References Cited

U.S. PATENT DOCUMENTS 6,053,913 A * 4/2000 Tu ...................... A61B 18/1206
600/585
2002/0029062 A1    3/2002 Satake
(Continued)

FOREIGN PATENT DOCUMENTS

JP    2000-225195 A    8/2000
JP    2002-78809 A     3/2002
(Continued)

*Primary Examiner* — Michael F Peffley
*Assistant Examiner* — Samantha M Good
(74) *Attorney, Agent, or Firm* — DLA Piper LLP (US)

(57) ABSTRACT

A balloon ablation catheter includes a catheter shaft containing a reinforcement wire in a thick section; a balloon provided at an end of the catheter shaft; and a high-frequency electric current electrode arranged in the balloon; which balloon ablation catheter satisfies L>t, wherein L represents the shortest distance from the surface of the reinforcement wire to the surface of the catheter shaft, and t represents the wall thickness of the thinnest portion of the balloon.

5 Claims, 3 Drawing Sheets

(52) U.S. Cl.
CPC ............... *A61B 2018/00285* (2013.01); *A61B 2018/044* (2013.01); *A61B 2018/046* (2013.01); *A61M 25/005* (2013.01); *A61M 25/0026* (2013.01)

(58) Field of Classification Search
CPC .... A61B 2018/0022; A61B 2018/0044; A61B 2018/0046; A61B 2018/00577
See application file for complete search history.

(56) References Cited

U.S. PATENT DOCUMENTS

| | | | |
|---|---|---|---|
| 2005/0203597 A1* | 9/2005 | Yamazaki | A61B 18/1492 607/98 |
| 2009/0157066 A1 | 6/2009 | Satake | |
| 2009/0204029 A1* | 8/2009 | Kassab | A61B 5/053 600/587 |
| 2010/0292687 A1* | 11/2010 | Kauphusman | A61B 17/12036 606/41 |
| 2012/0065633 A1 | 3/2012 | Yagi et al. | |
| 2012/0150107 A1* | 6/2012 | Cheung | A61M 25/1027 604/96.01 |

FOREIGN PATENT DOCUMENTS

| | | |
|---|---|---|
| JP | 2005-58509 A | 3/2005 |
| WO | 2004/017850 A1 | 3/2004 |
| WO | 2007/052341 A1 | 5/2007 |
| WO | 2010/113914 A1 | 10/2010 |

\* cited by examiner

BALLOON ABLATION CATHETER AND BALLOON ABLATION CATHETER SYSTEM

CROSS-REFERENCE TO RELATED APPLICATIONS

This application is a national stage application of International Application No. PCT/JP2014/059181, with an international filing date of Mar. 28, 2014, which designates the United States, incorporated herein by reference, and which claims the benefit of priority from Japanese Patent Application No. 2013-068479, filed Mar. 28, 2013, the entire contents of which are incorporated herein by reference.

TECHNICAL FIELD

This disclosure relates to a balloon ablation catheter and a balloon ablation catheter system.

BACKGROUND

A balloon ablation catheter is a medical device used to carry out ablation by heating a balloon arranged at the catheter tip.

For example, JP 2002-78809 A describes a balloon ablation catheter for electric pulmonary vein isolation in treatment of heart arrhythmia. That balloon ablation catheter is equipped with means for heating the balloon by allowing high-frequency current to flow between a counter electrode plate attached to the body surface of the patient and an electrode in the balloon. The heated balloon is brought into contact with an affected tissue to carry out treatment of the affected area.

Separately from a balloon ablation catheter, JP 2000-225195 A describes a catheter shaft in which a metal wire is installed. This catheter shaft has a metal-wire-based reinforcement layer installed on a tube, and the layer improves insertability and torque transmission performance of the body of the tube.

However, in the balloon ablation catheter described in JP 2002-78809 A, heating the balloon ablation catheter causes softening of the catheter shaft affected by the heat, which leads to elongation of the catheter shaft in the longitudinal direction under tensile strength to an extent where operation by the operator is adversely affected during use of the balloon ablation catheter, which is problematic.

A possible idea to suppress elongation of the catheter shaft in the longitudinal direction due to heating may be installation of a metal wire such as the one descried in JP 2000-225195 A in the catheter shaft. However, when high-frequency current is applied under conditions where the metal wire is installed, high-frequency current is generated in the metal wire in the catheter shaft, and this causes abnormal heating of the metal wire itself, making the operator or tissues other than the affected area in the patient to be burned, which is problematic.

It could therefore be helpful to provide a balloon ablation catheter wherein, even when the catheter shaft is heated by high frequency, elongation of the catheter shaft can be suppressed to an extent where the elongation does not adversely affect use of the balloon ablation catheter, and the risk of burning the operator or the patient caused by heating of the reinforcement wire in the catheter shaft can be largely reduced.

SUMMARY

We thus provide (1) to (7) below:

(1) A balloon ablation catheter comprising:
 a catheter shaft containing a reinforcement wire in a thick section;
 a balloon provided at an end of the catheter shaft; and
 a high-frequency electric current electrode arranged in the balloon;
 the balloon ablation catheter satisfying L>t, wherein L represents the shortest distance from the surface of the reinforcement wire to the surface of the catheter shaft, and t represents the wall thickness of the thinnest portion of the balloon.

(2) The balloon ablation catheter according to (1), wherein the wall thickness of the balloon is 20 to 150 µm.

(3) The balloon ablation catheter according to (1) or (2), wherein the reinforcement wire is a metal wire.

(4) The balloon ablation catheter according to any one of (1) to (3), wherein the reinforcement wire is installed to form a braid.

(5) The balloon ablation catheter according to any one of (1) to (3), wherein the reinforcement wire is linearly installed in the longitudinal direction of the catheter shaft.

(6) The balloon ablation catheter according to any one of (1) to (5), wherein the reinforcement wire is installed such that the reinforcement wire is not exposed from the distal end tip of the catheter shaft.

(7) A balloon ablation catheter system comprising:
 the balloon ablation catheter according to any one of (1) to (6);
 a counter electrode for transmitting high frequency to the high-frequency electric current electrode in the balloon; and
 a high-frequency power source for supplying high-frequency power to the counter electrode.

In the balloon ablation catheter, the catheter shaft is not elongated even under the influence of heat due to use of high frequency in combination, and flowing of high frequency through the reinforcement wire can be prevented.

DESCRIPTION OF SYMBOLS

Figure 1:
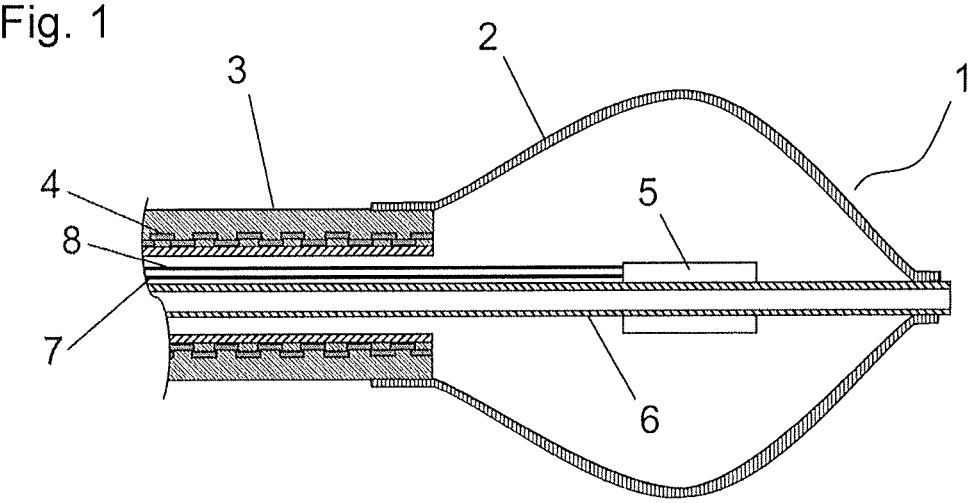
FIG. 1 is a longitudinal cross-sectional view of the tip section of a balloon ablation catheter according to a first example.

1, Balloon ablation catheter; 2, Balloon; 3, Outer cylinder shaft; 4, Reinforcement wire; 5, Electrode; 6, Inner cylinder shaft; 7, Electric wire; 8, Electric wire for a temperature sensor; 9, Inner layer tube; 10, Outer layer tube; 11, Multi-lumen shaft; 12, Water bath; 13, High-frequency power source; 14, Counter electrode plate; 15, Thermocouple; 16, Temperature measuring device

DETAILED DESCRIPTION

The balloon ablation catheter used to ablate an affected tissue using high frequency is characterized in that it has a catheter shaft containing a reinforcement wire in a thick section, a balloon provided at an end of the catheter shaft, and a high-frequency electric current electrode arranged in the balloon, which balloon ablation catheter satisfies L>t, wherein L represents the shortest distance from the surface of the reinforcement wire to the surface of the catheter shaft, and t represents the wall thickness of the thinnest portion of the balloon.

The "thick section" herein means the area surrounded by the outer surface of the catheter shaft excluding the area of the lumen portion, and corresponds to the thickness of the catheter shaft.

The "reinforcement wire" means a wire installed in the catheter shaft for reinforcement of the rigidity of the catheter shaft.

Preferred representative examples are described below in detail with reference to the drawings, but this disclosure is not limited to these examples. Each identical factor is represented using an identical symbol, and redundant explanations are omitted. The ratios used in the drawings are not necessarily the same as those in the description.

FIG. 1 is a longitudinal cross-sectional view of the tip section of a balloon ablation catheter according to a first example.

In FIG. 1, the balloon ablation catheter 1 has a double tube shaft 9 having an outer cylinder shaft 3 and an inner cylinder shaft 6; and a balloon 2. The balloon 2 has a spherical shape, and the outer cylinder shaft 6, which is a flexible tube, connects to the balloon 2 such that the tip of the outer cylinder shaft 6 connects to the opening in the base-end side of the balloon 2. The inner cylinder shaft 6, which is a flexible tube, passes through the inside of the balloon 2, and connects to the opening in the tip side of the balloon 2. By this, the balloon 2 is tightly sealed. An electrode 5 is placed on the inner cylinder shaft 6 in the balloon 2, and the electrode 5 connects to a high-frequency power source not shown in the figure through an electric wire 7. In addition, an electric wire 8 for a temperature sensor connects to the electrode 5, and the electrode 5 also plays a role as a temperature sensor. The electrode 5 is arranged near the longitudinal center of the balloon so that the temperature in the balloon 2 can be measured.

Figure 2:
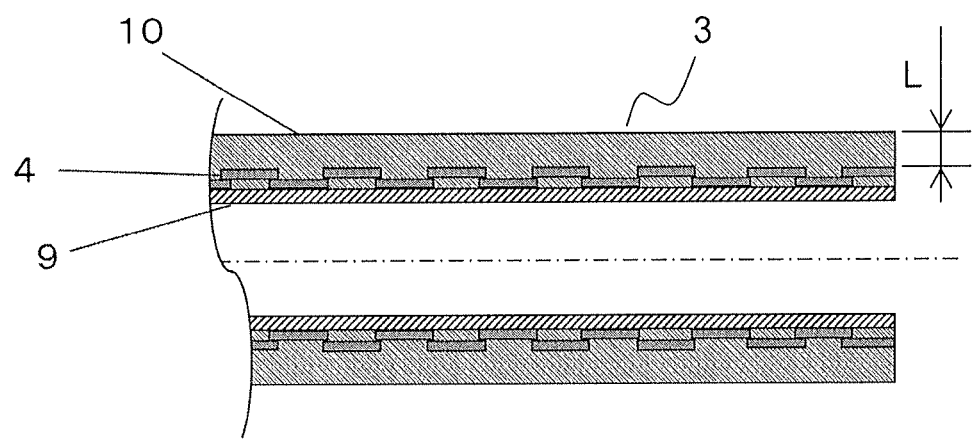
FIG. 2 is a plan view showing the thick section of the catheter shaft of the balloon ablation catheter according to the first example.

FIG. 2 is a schematic diagram showing a longitudinal cross-sectional view of the outer cylinder shaft contained in the balloon ablation catheter according to the first example. The thick section of the outer cylinder shaft 3 in FIG. 1 is constituted of a portion having a thickness with a three-layer structure from the surface of the lumen of an inner layer tube 9 to the surface of the outer layer of an outer layer tube 10, wherein a reinforcement wire 4 is sandwiched therebetween. In this case, the distance L represents the distance from the outermost surface in the outer layer side of the reinforcement layer 4 to the surface of the outer layer tube 10.

Figure 3:
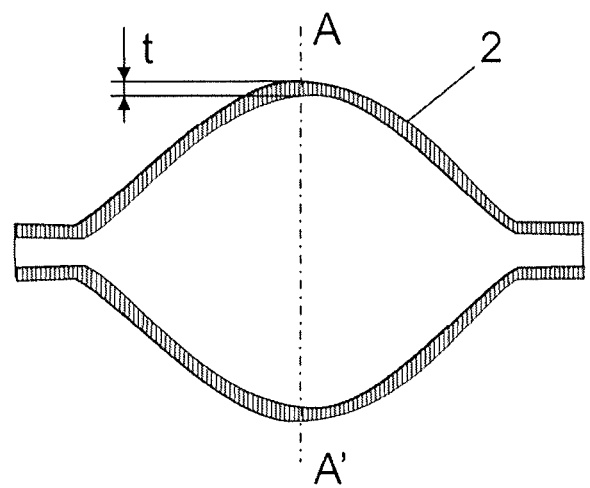
FIG. 3 is a plan view showing the balloon of a balloon ablation catheter according to a second example.

FIG. 3 is a schematic diagram showing a longitudinal cross-sectional view of the balloon contained in the balloon ablation catheter according to the first example. In FIG. 3, the wall thickness of the thinnest portion in the balloon 2 is defined as the wall thickness t. In this example, the wall thickness on the A-A' plane, where the diameter of the balloon in the direction vertical to the longitudinal direction is largest, is the wall thickness t.

In this example, the reinforcement wire 4 is arranged such that L is larger than the wall thickness t. By this, when high frequency is transmitted from a counter electrode not shown in the figure to the balloon, the high frequency is more likely to flow to the electrode 5 in the balloon 2 than to the reinforcement wire 4 so that heating of the reinforcement wire 4 can be prevented.

The material of the balloon 2 may be any material as long as the material is one which is used for medical catheters. From the viewpoint of achievement of increased adhesion to the affected tissue, the material is preferably an elastic material such as a polyurethane or a rubber, for example, a synthetic rubber or a natural rubber. The wall thickness of the balloon 2 is preferably 20 to 150 µm, more preferably 20 to 100 µm, from the viewpoint of achievement of better adhesion to the affected tissue.

The outer diameter of the balloon 2 varies depending on the affected area to which the operational technique is applied. For example, in cases of treatment of arrhythmia, the outer diameter is preferably 20 to 40 mm. The balloon 2 preferably has a spherical shape, but may also have a tapered conical shape. The shape of the balloon 2 is not limited to these.

The material of the outer cylinder shaft 3 and the inner cylinder shaft 6 may be any material as long as the material is one which is used for medical catheters. Examples of the material include polymer materials having flexibility such as polyamide resins and polyamide elastomers including nylon 11 and nylon 12; polyolefins including polypropylene/polyethylene; polyesters including polyethylene terephthalate; polyurethane; and vinyl chloride. One of these, or a combination of two or more of these may be used.

An imaging substance such as barium sulfate or bismuth subcarbonate may be included in the material of the outer cylinder shaft 3 and the inner cylinder shaft 6 to increase the imaging ability in X-ray.

In this example, the catheter shaft has a double-tube structure composed of an outer cylinder shaft and an inner cylinder shaft. However, the catheter shaft may also be in a multi-lumen shape.

Figure 4:
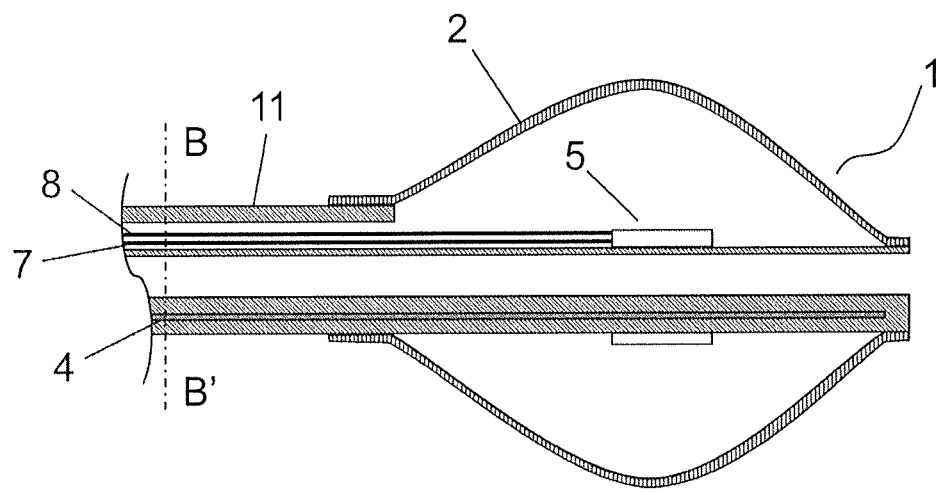
FIG. 4 is a longitudinal cross-sectional view of the tip section of a balloon ablation catheter according to the second example.

FIG. 4 is a longitudinal cross-sectional view of a balloon ablation catheter according to a second example. In the second example, a multi-lumen shaft 11 is used instead of the shaft having a double-tube structure. In the second example, the reinforcement wire 4 is linearly installed along the longitudinal direction of the multi-lumen shaft 11 in the thick section of the multi-lumen shaft 12.

Figure 5:
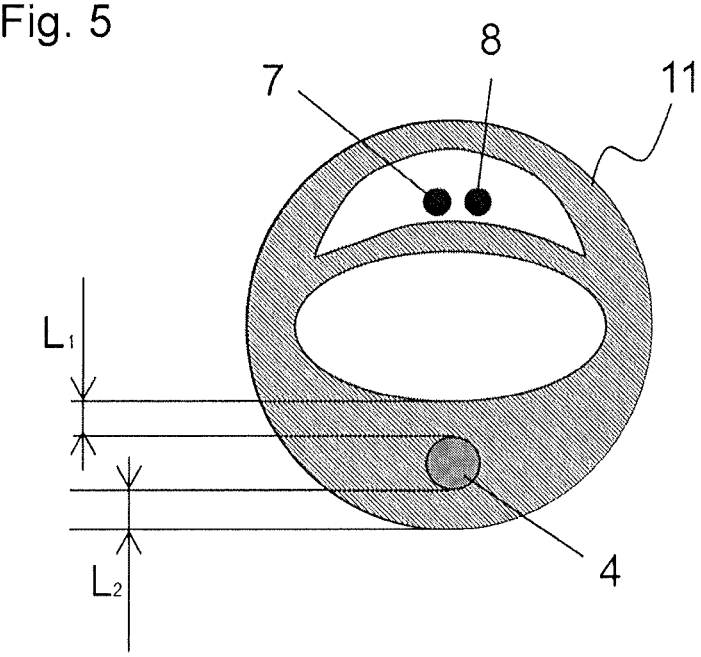
FIG. 5 is a cross-sectional view of the multi-lumen shaft shown in FIG. 4 taken on the B-B' plane, which is in the direction vertical to the longitudinal direction of the shaft.

FIG. 5 is a cross-sectional view of the multi-lumen shaft 12 shown in FIG. 4 taken on the B-B' plane, which is in the direction vertical to the longitudinal direction of the shaft. When the multi-lumen shaft 12 is used, the thick section corresponds to the thickness from an inner cavity, lumen, to the surface of the outer layer of the shaft, wherein the reinforcement wire 4 is sandwiched therebetween. The distance L can be interpreted in two ways—that is, $L_1$, the shortest distance from the surface of the reinforcement wire 4 to the surface of the lumen of the multi-lumen shaft 12, and $L_2$, the shortest distance from the surface of the reinforcement wire 4 to the outer surface of the multi-lumen shaft 12. When the shorter distance selected from $L_1$ and $L_2$ is longer than the wall thickness of the balloon 2, t, heating of the reinforcement wire 4 can be prevented.

The material of the reinforcement wire 4 may be an aramid yarn or a nylon yarn, a carbon fiber, or a metal wire. In view of increasing the tension resistance, rigidity, and corrosion resistance, a metal wire of SUS, NiTi alloy, or platinum is preferably used. To make high frequency less likely to pass through the reinforcement wire 4, the reinforcement wire is preferably arranged such that the reinforcement wire is not exposed from the distal end tip of the catheter shaft.

The cross-sectional shape of the reinforcement wire 4 is not limited. When the wire has a rectangular cross section, when the reinforcement wire 4 is installed to form a braid, the friction increases due to an increase in the contacting area among reinforcement wires 4 so that elongation of the catheter shaft can be better reduced.

The material of the electrode 5 and the electric wire 7 may be any metal as long as the metal allows electric transmission. A highly conductive electric wire of copper, silver, gold, platinum, tungsten, an alloy, or the like is preferably used. For temperature measurement, the metal for the electric wire 8 for a temperature sensor needs to be different from that of the electric wire 7. Preferably, the electric wire 7 is a copper wire, and the electric wire 8 for a temperature sensor is a constantan wire. However, the electric wires are not limited to these.

In the second example, the electric wire 7 plays roles both as an electric wire that transmits high-frequency current and as an electric wire for formation of a thermocouple. Alternatively, the electric wire that transmits high-frequency current and the electric wire for a thermocouple may be separately provided.

EXAMPLES

Specific examples of the balloon ablation catheter are concretely described below with reference to figures.

Example 1

A balloon 2 was provided as a spherical balloon wherein the wall thickness at the thinnest portion is 40 μm; the outer balloon diameter is 25 mm; the neck portion at the base-end section of the balloon has a longitudinal length of 10 mm, an outer diameter of 3.6 mm, and an inner diameter of 3.1 mm; and the neck portion at the tip section of the balloon has a longitudinal length of 10 mm, an outer diameter of 2 mm, and an inner diameter of 1.6 mm. The balloon 2 was prepared by blow molding using a urethane material.

On an inner layer tube 9 made of a PTFE material having an inner diameter of 2.5 mm and a thickness of 50 μm, an SUS plate reinforcement wire 4 having a thickness of 60 μm and a width of 190 μm was arranged in a mesh-like shape along the longitudinal direction of the inner layer tube 9. The reinforcement wire was further covered with a polyurethane material such that the outer diameter was 3.1 mm to form an outer layer tube 10, thereby preparing an outer cylinder shaft 3 having a three-layer structure.

As a result, the outer cylinder shaft 3 was provided as a single-lumen catheter shaft having an inner diameter of 2.5 mm, an outer diameter of 3.1 mm, a thickness of 300 μm, and a length of 900 mm, wherein the shortest distance from the surface of the reinforcement wire 4 to the surface of the outer cylinder shaft 3 is 130 μm.

The inner cylinder shaft 6 was prepared using nylon as a material such that a single-lumen shaft having an inner diameter of 1.2 mm and an outer diameter of 1.6 mm was provided. As the electrode 5, a copper wire subjected to silver plating having a wire diameter of 30 μm was used, and the wire was wound around the inner cylinder shaft 6 into a coil shape from the position 20 mm distant from the tip of the inner cylinder shaft 6 toward the base end in the longitudinal direction along a distance of 10 mm.

During the winding of the electrode 5 around the inner cylinder shaft 6 into a coil shape, a constantan electric wire 8 with a wire diameter of 25 μm for a temperature sensor was folded together to form a thermocouple. In the copper wire used as the electrode 5, the coil end of the electrode 5 was linearly extended in the longitudinal direction toward the base end of the inner cylinder shaft 6 to use the copper wire also as the electric wire 7.

The inner cylinder shaft assembly prepared as described above by combining the inner cylinder shaft 6 with the electrode 5, the electric wire 7, and the electric wire 8 for a temperature sensor was inserted into the outer cylinder shaft 3 such that the assembly protrudes 35 mm from the outer cylinder shaft 3 toward the tip side in the longitudinal direction. The neck portion in the base-end side in the longitudinal direction of the balloon 2 was adhered to the outer cylinder shaft 3 under heat, and the neck portion in the tip side in the longitudinal direction of the balloon 2 was adhered to the inner cylinder shaft 6 under heat, to prepare a balloon ablation catheter 1.

Comparative Example 1

For comparison with Preparation Example 1 in terms of elongation of the balloon ablation catheter, an ablation catheter was prepared such that the catheter has the same constitution as that of Preparation Example 1 except that the reinforcement wire 4 was not installed in the outer cylinder shaft 3, and that a single-lumen catheter shaft was prepared using a polyurethane member tube having an inner diameter of 2.5 mm, an outer diameter of 3.1 mm, and a length of 900 mm.

Comparative Example 2

For comparison with Preparation Example 1 in terms of heat generation from the balloon ablation catheter, an outer cylinder shaft 3 was prepared as follows. Tubing was carried out with a polyurethane member such that the inner diameter was 2.5 mm and the thickness was 180 μm, and an SUS reinforcement wire 4 having a wire diameter of 40 μm was linearly arranged thereon along the longitudinal direction, followed by carrying out tubing thereon with the same polyurethane member such that the outer diameter was 3.0 mm, to prepare the outer cylinder shaft.

The obtained outer cylinder shaft 3 had an inner diameter of 2.5 mm, an outer diameter of 3.0 mm, a thickness of 250 μm, and a length of 900 mm. A single-lumen catheter shaft in which the shortest distance from the surface of the reinforcement wire 4 to the surface of the outer cylinder shaft 3 was 30 μm was prepared. Other constitutions were the same as those of Preparation Example 1.

Elongation Test

The balloon ablation catheters prepared in Example 1 and Comparative Example 1 were immersed in warm water at 37° C. for 2 hours. Subsequently, while the tip in the longitudinal direction of the outer cylinder shaft of each catheter was held with a hand, weight was applied by giving a 7-kg weight to the posterior end in the longitudinal direction of the outer cylinder shaft for a sufficient time. Thereafter, elongation of the outer cylinder shaft was compared.

As a result of the elongation test, the outer cylinder shaft of the balloon ablation catheter of Preparation Example 1 elongated from 900 mm to 901 mm, and the outer cylinder shaft 3 did not cover the electrode 5. Thus, usefulness of the balloon ablation catheter could be maintained in this case. On the other hand, the outer cylinder shaft of the balloon ablation catheter of Comparative Example 1 elongated from 900 mm to 910 mm, and the outer cylinder shaft 3 covered most part of the electrode 5. Thus, use of the balloon ablation catheter became difficult in this case.

From the results of the elongation test, it is clear that our balloon ablation catheter prevents elongation of the outer cylinder shaft.

Heat Generation Test

For comparison of the heat generating property between Example 1 and Comparative Example 2, high-frequency power was supplied to the balloon ablation catheters prepared in Example 1 and Comparative Example 2, and the surface temperature of the catheter shaft was compared between these.

Figure 6:
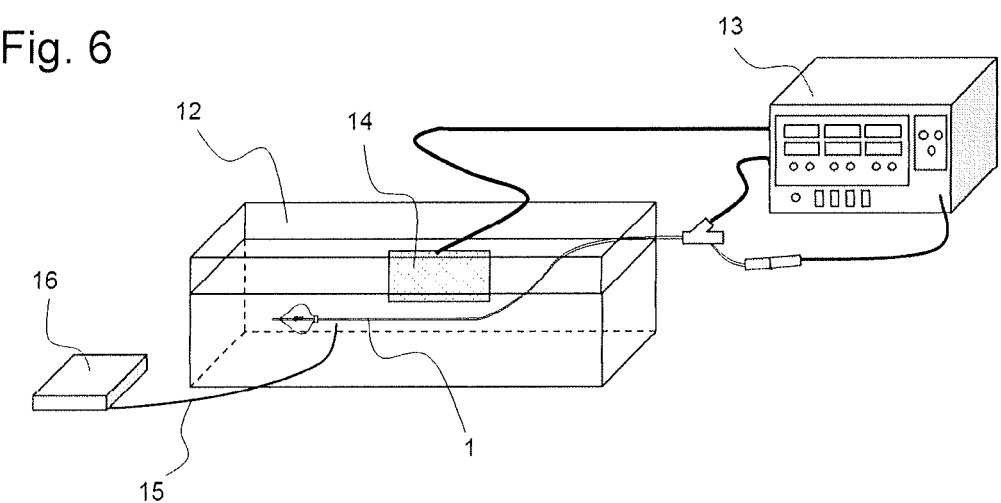
FIG. 6 is a schematic view of a shaft heat generation test system.

FIG. 6 shows a schematic view of a catheter shaft heat generation test system.

In a water bath 12 filled with 0.9% physiological saline at 37° C., a counter electrode plate 14 connected to a high-frequency power source 13 was placed, and the ablation catheters of Example 1 and Comparative Example 2 were immersed in the water bath 12. The electric wire 7 and the electric wire 8 for a temperature sensor were connected to the high-frequency power source 14. On the surface of the outer cylinder shaft 3 in the vicinity of the balloon of the balloon ablation catheter 1, a thermocouple 15 was attached, and the temperature during application of high-frequency current was measured by a temperature measuring device 16.

The balloons 2 of Example 1 and Comparative Example 2 were inflated to an outer diameter of 25 mm by injection of 50% dilution of a contrast medium (ioxaglate injection; trade name, Hexabrix 320) in physiological saline into the balloons 2.

To investigate the surface temperature of the outer cylinder shaft 3 during the application of high-frequency current, the thermocouple was placed at the position 15 mm distant from the tip of the outer cylinder shaft 3.

The frequency of the high-frequency power source was set to 1.8 Mhz, and the temperature in the balloon 2 was set to 70° C. As a result of application of high frequency for 5 minutes, the measured surface temperature of the outer cylinder shaft 3 was 39° C. in Example 1. On the other hand, in Comparative Example 2, the measured surface temperature of the outer cylinder shaft 3 was 51° C.

From the results of the heat generation test, it is clear that our balloon ablation catheter prevents generation of heat from the outer cylinder shaft.

INDUSTRIAL APPLICABILITY

Our catheters can be used as a balloon ablation catheter and as a balloon ablation catheter system to ablate an affected target area.

The invention claimed is:

1. A balloon ablation catheter comprising:
a catheter shaft comprising an outer layer tube, an inner layer tube and a metal reinforcement wire sandwiched between the outer layer tube and the inner layer tube;
a balloon provided at a distal terminus of said outer layer tube; and
a high-frequency electric current electrode arranged in said balloon;
said balloon ablation catheter satisfying L>t, wherein L represents a shortest distance from a surface of said reinforcement wire to a surface of said catheter shaft, and t represents wall thickness of a thinnest portion of said balloon,
wherein said reinforcement wire is installed such that said reinforcement wire is not exposed from a distal end tip of said catheter shaft.

2. The balloon ablation catheter according to claim 1, wherein the wall thickness of said balloon is 20 to 150 μm.

3. The balloon ablation catheter according to claim 1, wherein said reinforcement wire is installed to form a braid.

4. The balloon ablation catheter according to claim 1, wherein said reinforcement wire is linearly installed in a longitudinal direction of said catheter shaft.

5. A balloon ablation catheter system comprising:
the balloon ablation catheter according to claim 1;
a counter electrode that transmits high frequency to said high-frequency electric current electrode in said balloon; and
a high-frequency power source that supplies high-frequency power to said counter electrode.

\* \* \* \* \*